United States Patent
Kosecoff

(10) Patent No.: US 11,893,826 B2
(45) Date of Patent: Feb. 6, 2024

(54) DETERMINING POSITION OF A PERSONAL CARE DEVICE RELATIVE TO BODY SURFACE

(71) Applicant: L'Oreal, Paris (FR)

(72) Inventor: David B. Kosecoff, San Francisco, CA (US)

(73) Assignee: L'Oreal, Paris (FR)

( * ) Notice: Subject to any disclaimer, the term of this patent is extended or adjusted under 35 U.S.C. 154(b) by 497 days.

(21) Appl. No.: 17/214,414

(22) Filed: Mar. 26, 2021

(65) Prior Publication Data

US 2022/0309269 A1 Sep. 29, 2022

(51) Int. Cl.
G06K 9/00 (2022.01)
G06V 40/16 (2022.01)
G16H 30/00 (2018.01)
G16H 20/00 (2018.01)
G06V 10/20 (2022.01)

(52) U.S. Cl.
CPC .............. *G06V 40/16* (2022.01); *G06V 10/20* (2022.01); *G16H 20/00* (2018.01); *G16H 30/00* (2018.01)

(58) Field of Classification Search
None
See application file for complete search history.

(56) References Cited

U.S. PATENT DOCUMENTS

| | | | |
|---|---|---|---|
| 10,004,885 B2 | 6/2018 | Casasanta, III et al. |
| 10,071,233 B2 | 9/2018 | Casasanta, III et al. |
| 10,076,646 B2 | 9/2018 | Casasanta, III et al. |
| 10,188,192 B2 | 1/2019 | Rabe et al. |
| 10,188,193 B2 | 1/2019 | Rabe et al. |
| 2011/0124989 A1 | 5/2011 | Edgar et al. |

(Continued)

FOREIGN PATENT DOCUMENTS

| | | |
|---|---|---|
| WO | 2008052348 A1 | 5/2008 |
| WO | 2016071325 A1 | 5/2016 |

(Continued)

OTHER PUBLICATIONS

Opte: Beauty Device for Age Spot Removal & Facial Toning, 2020 Proctor & Gamble, <https://www.opteskin.com> [retrieved Jul. 21, 2020], pp. 1-12 (Year: 2020).*

(Continued)

*Primary Examiner* — Tuan S Nguyen
(74) *Attorney, Agent, or Firm* — CHRISTENSEN O'CONNOR JOHNSON KINDNESS PLLC

(57) ABSTRACT

A computer system obtains a digital 3-dimensional model of a body surface, such as a human face. Portions of the surface correspond to reference points in the model. The system obtains image data of a personal care device in use as well as image data of the surface on which the model is based. The system calculates a relative location of the device relative to the reference points based on the image data of the surface. The system determines a true position of the device with respect to the surface based on the image data of the device in use, known physical dimensions of the device, and its relative location, even when the device is partially occluded from view. The system may, based on the true position of the device, cause device to perform actions such as application of a cosmetic or administration of a skin therapy.

20 Claims, 5 Drawing Sheets

(56) References Cited

U.S. PATENT DOCUMENTS

| | | |
|---|---|---|
| 2011/0155161 A1 | 6/2011 | Samain |
| 2014/0160123 A1* | 6/2014 | Yang .................. G06T 17/00 345/420 |
| 2018/0369077 A1 | 12/2018 | Giron et al. |
| 2018/0369078 A1 | 12/2018 | Giron et al. |
| 2020/0167983 A1 | 5/2020 | Iglehart et al. |
| 2020/0337444 A1* | 10/2020 | Samain ................ B29C 64/393 |

FOREIGN PATENT DOCUMENTS

| | | | | |
|---|---|---|---|---|
| WO | WO-2016071325 A1 * | 5/2016 | ........... | A61B 18/203 |
| WO | 2020145826 A1 | 7/2020 | | |
| WO | WO-2020145826 A1 * | 7/2020 | ............. | A61B 34/10 |

OTHER PUBLICATIONS

Written Opinion and Search Report dated Mar. 30, 2022, issued in corresponding French Application No. FR2107993 (French version) filed Jul. 23, 2021, 7 pages.

Opte: Beauty Device for Age Spot Removal & Facial Toning, © 2020 Procter & Gamble, <https://www.opteskin.com> [retrieved Jul. 21, 2020], pp. 1-12.

X-Guide ™: Nobel Biocare United States, © 2021 Nobel Biocare Services, <https://www.nobelbiocare.com/en-us/x-guide> [retrieved Feb. 17, 2021], pp. 1-6.

Prinker Manual, screen shots of video manual <https://www.prinker.net/manual/prinker-s> [retrieved Mar. 25, 2021], 3 pages.

CNET, "Pass this temporary tattoo machine over your arm for instant ink", <https://www.cnet.com/news/pass-this-temporary-tattoo-machine-over-your-arm-for-instant-ink/> [retrieved Mar. 18, 2021], 3 pages.

* cited by examiner

DETERMINING POSITION OF A PERSONAL CARE DEVICE RELATIVE TO BODY SURFACE

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a computer system obtains a digital 3-dimensional model of a human body surface, such as a face or other region of interest. Portions of the body surface correspond to reference points in the 3-dimensional model. The system obtains image data of a personal care device having known physical dimensions and image data of the body surface on which the 3-dimensional model is based. The system calculates a relative location of the personal care device relative to the reference points based at least in part on the image data of the body surface. The system determines a true position of the personal care device with respect to the body surface based at least in part on the image data of the personal care device, the known physical dimensions of the personal care device, and the relative location of the personal care device. This allows the system to obtain the true position of a personal care device relative to a human body surface even when the personal care device is partially occluded from view. Embodiments disclosed herein are useful in many scenarios such as computer-guided cosmetics application, computer-guided skin therapies, and the like.

In some embodiments, the image data of the human body surface is obtained from one or more image sensors separate from the personal care device, from one or more image sensors mounted on the personal care device, or a combination thereof.

In some embodiments, the calculating of the relative location of the personal care device is further based on depth data obtained from one or more depth sensors, or proximity data obtained from one or more proximity sensors, or a combination thereof.

In some embodiments, the computer system causes an interaction of the personal care device with the human body surface based on the true position of the personal care device. In an embodiment, the interaction includes application of a cosmetic product to the body surface. In another embodiment, the interaction includes administration of a skin therapy (e.g., phototherapy, a cleansing therapy, etc.) on the body surface. In an embodiment, the interaction occurs as the personal care device is in motion. In an embodiment, the interaction occurs as the personal care device is in contact with or within a predetermined distance of the human body surface. In an embodiment, the computer system determines whether the personal care device is in contact or within a predetermined distance based on data received from a proximity sensor.

In some embodiments, the computer system detects one or more skin features (e.g., wrinkles, blemishes, visible pores, areas of hyperpigmentation, etc.) at the corresponding portion of the human body surface based at least in part on the image data. In an embodiment, the computer system adds representations of such features to a map of skin features.

In some embodiments, a personal care device includes one or more sensors, a processor, and memory, the memory having stored therein computer-executable instructions configured to cause the personal care device to perform steps comprising obtaining, via the one or more sensors, sensor data with respect to a human body surface on which a digital 3-dimensional model is based, wherein portions of the human body surface correspond to reference points in the digital 3-dimensional model; calculating a relative location of the personal care device relative to the reference points in the digital 3-dimensional model based at least in part on the sensor data obtained via the one or more sensors; and determining a true position of the personal care device with respect to the human body surface based at least in part on image data of the personal care device in use, known physical dimensions of the personal care device, and the relative location of the personal care device.

In an embodiment, the one or more sensors include a depth sensor, and the detecting of the relative location of the personal care device is based on depth data obtained from the depth sensor. In an embodiment, the one or more sensors include a camera, and wherein the detecting of the relative location of the personal care device is based on image data obtained from the camera. In an embodiment, the computer-executable instructions are further configured to cause the personal care device to perform one or more actions based on the true position of the personal care device, such as application of a cosmetic product, or detection of a skin feature, or administration of a therapy at a corresponding portion of the human body surface.

In some embodiments, a computer system obtains image data of a personal care device and image data of a human body surface; generates a digital representation on a display of a 3-dimensional model including a plurality of reference locations on the human body surface based at least in part on the image data of the human body surface; determines a relative location of the personal care device relative to the plurality of reference locations on the human body surface; and generates a digital representation of a true position of the personal care device with respect to the human body surface based at least in part on the image data of the personal care device, pre-determined physical dimensions of the personal care device, and the relative location of the personal care device.

In some embodiments, a system comprises a surface features unit operably coupled to a plurality of sensors, the surface features unit including computational circuitry and at least one processor configured to obtain sensor data with respect to a human body surface, and generate a digital representation on a display of a 3-dimensional model including a plurality of reference locations on a human body surface; and a locator unit operably coupled to the surface features unit and a personal care device. The locator unit includes computational circuitry and at least one processor configured to determine a location of a personal care device relative to one or more of the plurality of reference locations on the human body surface; and determine a true position of the personal care device relative to the human body surface based at least in part on image data of the personal care device in use, pre-determined physical dimensions of the personal care device, and the relative location of the personal care device.

In an embodiment, the locator unit operably coupled to the surface features unit and the personal care device includes computational circuitry and at least one processor configured to determine the orientation of the personal care device relative to one or more of the plurality of reference locations on the human body surface based at least in part on image data of the personal care device in use, pre-determined physical dimensions of the personal care device, and the relative location of the personal care device. In an embodiment, true position information includes personal care device orientation and one or more of the plurality reference locations on the human body surface.

In an embodiment, the locator unit operably coupled to the surface features unit and the personal care device includes computational circuitry and at least one processor configured to determine relative movement information of the personal care device relative to one or more of the plurality of reference locations on the human body surface based at least in part on image data of the personal care device in use, pre-determined physical dimensions of the personal care device, and the relative location of the personal care device.

In an embodiment, true position information includes personal care device movement information and one or more of the plurality reference locations on the human body surface.

BRIEF DESCRIPTION OF THE DRAWINGS

The foregoing aspects and many of the attendant advantages of the present disclosure will become more readily appreciated as the same become better understood by reference to the following detailed description, when taken in conjunction with the accompanying drawings, wherein.

DETAILED DESCRIPTION

Figure 1:
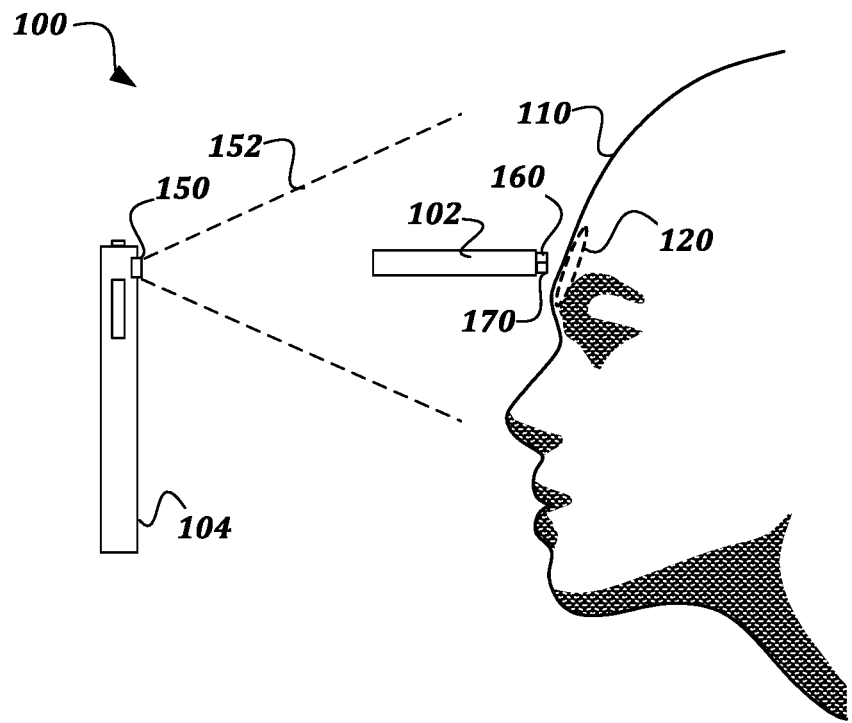
FIG. 1 is a schematic illustration of an embodiment of a system that uses sensor data to determine the true position of a personal care device in use in relation to a human face, according to various aspects of the present disclosure.

In embodiments disclosed herein, techniques are described for determining where a personal care device is relative to a body surface, such as a subject's face or other region of interest, using one or more cameras and/or other sensors. Described embodiments use image sensors to determine a relative location of the personal care device relative to reference points while also maintaining anatomical awareness, determine the true position (e.g., location and/or orientation) of the personal care device with respect to a human body surface of interest. Described embodiments are useful in many contexts, including cosmetics or body art applications, skin feature mapping or monitoring, dermato-logical diagnosis or treatments, or telehealth applications. In the context of such applications, described embodiments provide precision and greater ease of use over complex manual routines.

Sensors suitable for use in described embodiments include 2-dimensional (2D) or 3-dimensional (3D) cameras, proximity sensors, or other integrated or peripheral cameras or sensors. Depth sensors are used in some embodiments to obtain 3D information about surfaces and include a range of possible hardware suitable for this purpose, including RGB or infrared stereoscopic cameras, laser or infrared LiDAR sensors, and dot projectors.

3D scans enable improved measurement of actual dimensions of a body surface and allow depth sensing, which can help to determine, for example, how far the body surface is from the camera, or detailed information about particular skin features, such as wrinkles. Reference points obtained through high-quality 3D scanning in accordance with described embodiments provides greater accuracy for determining location than traditional reference points obtained with 2D imaging, such as eyes, lips, noses, or other prominent facial features, and are particularly helpful where the region of interest is occluded.

In described embodiments, a far-field camera unit captures a target body surface at a distance that allows the body surface to be mapped and navigated. In an embodiment, the far-field camera unit includes camera hardware integrated in a mobile computing device such as a smartphone or tablet computer with corresponding image processing software, such as a TrueDepth camera available from Apple Inc. Alternatively, far-field imaging is provided by one or more external cameras in communication with a computing device, by a large in-store "scanning booth" including multiple cameras, or in some other way.

The personal care device may be configured to dispense a cosmetic, perform a therapy, capture an image, or perform some other action at a precise location on a body surface (e.g., skin, nails, hair, etc.) and/or a precise moment as the device is moving. The system maintains awareness of the face or other body part of interest to achieve anatomical awareness as well as tracking the position of the personal care device relative to the body surface. This allows the action to be performed at a precise location on the body.

In an embodiment, a smartphone camera or other external camera may be used to track the position of the personal care device relative to a region of interest. Anatomical location awareness may also be provided by a camera mounted on the personal care device itself, at a sufficient distance to maintain a view of the personal care device and the region of interest.

In an embodiment, the personal care device is a registered object in a digital 3D environment with known, pre-determined spatial dimensions that are used to track the position of the personal care device, even in cases where the personal care device is partially occluded from view. In such an embodiment, the physical dimensions of the personal care device are provided to the computer system ahead of time. Thus, even in cases where the personal care device is partially occluded from view, the true position (e.g., location and orientation) of the personal care device can be calculated based on the known physical dimensions of the device and the relative location relative to the reference points. The ability to determine the true position of a personal care device relative to a human body surface is useful in many scenarios such as computer-guided cosmetics application, computer-guided skin therapies, and the like.

In some embodiments, the computer system causes an action by the personal care device based on the determined true position, such as application of cosmetics products or administration of a skin therapy (e.g., a phototherapy, a cleansing therapy, etc.). In an embodiment, the action occurs as the personal care device is in motion.

In some embodiments, the computer system detects one or more skin features (e.g., wrinkles, blemishes, visible pores, areas of hyperpigmentation, etc.) based at least in part on the image data. In an embodiment, the computer system adds representations of such features to a map of skin features. Mapping of skin features is useful, for example, to identify changes in skin conditions (e.g., changes in moles, skin pigmentation, skin texture, etc.), which can be helpful in diagnosis of dermatological conditions or for tracking progress of a skin care regimen to improve skin tone, reduce blemishes or acne lesions, minimize the appearance of wrinkles, or for other purposes.

The system is capable of working with digital 3D models obtained in different ways. In an embodiment, the digital 3D model is created based on image data and depth data captured by sensors separate from the personal care device. In other embodiments, the 3D model is created based on image data and depth data captured by sensors mounted on the personal care device or, in a hybrid approach, by a combination of sensors mounted on and separate from the personal care device. In an illustrative hybrid approach, far-field image sensors track the anatomical position of the personal care device, while near-field sensors on the personal care device capture detailed images of the body surface. The detailed data captured by the near-field sensors of the personal care device can then be assembled into a 3D model with reference to the positional data obtained by the far-field sensors.

FIG. 1 is a schematic illustration of a non-limiting example embodiment of a system 100 that uses sensor data to determine the true position of a personal care device in use, in relation to a human face, according to various aspects of the present disclosure. A camera unit 150 of a client computing device 104 includes one or more cameras and captures images of a personal care device 102 (e.g., a cosmetic applicator device, a skin therapy device, etc.) in relation to a subject's face 110. In the example shown in FIG. 1, the client computing device 104 is a mobile computing device such as a smartphone or tablet computer. The personal care device includes a skin interaction unit 160, such a cosmetics application unit, and one or more sensors 170. In an embodiment, the sensor(s) 170 include one or more image sensors, a proximity sensor, a contact sensor, a depth sensor, or a combination thereof. In an embodiment, the sensors 170 of the personal care device include one or more near-field image sensors to capture body surface features at a greater level of detail.

In an illustrative scenario, the camera unit 150 acts as a far-field camera positioned and configured to capture video or still images of the personal care device 102 in use, as well a region of interest 120 of the subject's face, such that the personal care device 102 and the region of interest 120 are within the field of view 152 of the camera unit 150. In the example shown in FIG. 1, the back end of the personal care device 102 is visible in the field of view 152 while other portions are occluded, including the front end on which the skin interaction unit 160 and sensor(s) 170 are mounted.

In an embodiment, the camera unit 150 is maintained in a fixed position while the personal care device 102 is in motion. In an embodiment, the camera unit 150 includes more than one camera, such as for stereoscopic video capture and/or depth sensing. In an embodiment, the camera unit 150 also includes one or more sensors other than cameras (e.g., a LiDAR sensor or infrared dot projector for depth sensing, a proximity sensor for proximity detection, etc.). In an embodiment, an infrared dot projector projects infrared dots onto a surface, and reflections from the surface are measured by an infrared camera to determine the distance each dot is from the projector system. When working in conjunction with a 3D camera, these depth measurements can be mapped onto a captured 3D image. This approach is used in some embodiments to generate a 3D model of a body surface, and for real-time tracking of additional surface points that are less prominent than, say, eyes or mouth.

Figure 2:
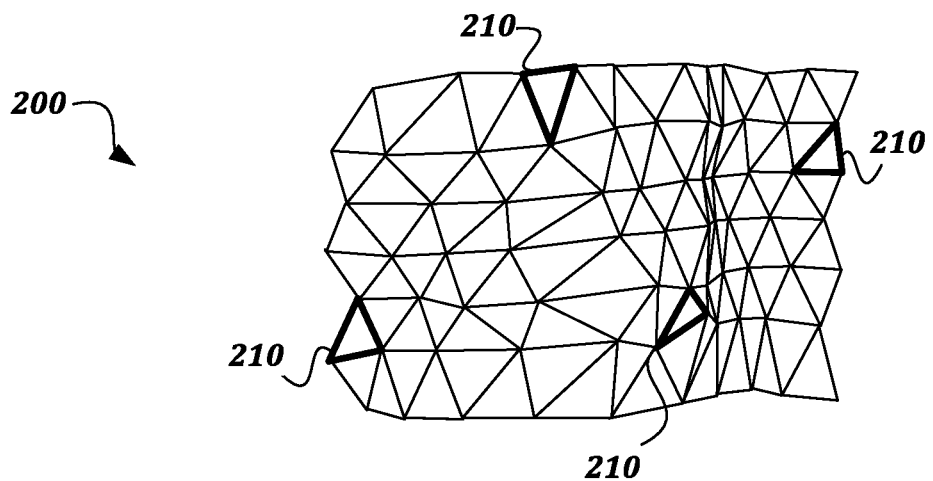
FIG. 2 is a schematic illustration of a 3-dimensional model portion implemented as a triangle mesh structure with reference points for determining a location of a personal care device, according to various aspects of the present disclosure.

The system 100 calculates a relative location of the personal care device 102 by comparing captured image data with corresponding reference points in a digital 3D model of the subject's face 110. FIG. 2 is a schematic illustration of a 3D model portion 200 implemented as a triangle mesh structure. In the illustrative arrangement shown in FIG. 1, the personal care device 102 is positioned near a region of interest 120 between the user's eyes. The 3D model portion 200 corresponds to the region of interest 120. The 3D model portion 200 includes several reference points 210 in the form of corresponding triangles of the mesh structure with distinctive texture mapping that represents a particular portion of skin in the region of interest 120, including a vertical "frown line" or glabellar line. In the example shown in FIG. 1, the system 110 compares data captured by the camera unit 150 of the client computing device 104 with texture data mapped to the reference points 210, and calculates the relative position of the personal care device relative to those reference points.

As noted above, some portions of the personal care device 102 are occluded from view, including the front end portion on which the interaction unit 160 and sensor(s) 170 are mounted, which faces away from the camera unit 150. In some embodiments, the system 100 is capable of recognizing the personal care device 102 via image obtained captured by the camera unit 150. This recognition may include detecting a graphical code, such as a QR code, on the personal care device 102, or using other computer vision techniques, such as object recognition. Even if the system 100 has located the back end portion of the personal care device and has calculated a relative location of the personal care device 102 relative to the reference points, the system 100 may not know the true position of the personal care device 102 relative to the body surface 110, including how far the interaction unit 160 or front end portion of the personal care device 102 is from the body surface 110, unless the dimensions of the personal care device 102 are known. If the true position is not known, the system may be unable to accurately determine when an interaction with the body surface 110 can be effectively and accurately performed. Accordingly, in some embodiments, the system 100 obtains known physical dimensions of the personal care device 102 (e.g., from memory in the client computing device 104 or some other source) and uses this information in combination with the relative location of the personal care device 102 to calculate its true position.

In some scenarios, such as where greater precision in determining position or surface modeling is desired, data captured by the camera unit 150 of the client computing device 104 is supplemented with data captured by sensor(s) 170 of the personal care device. In an embodiment, the sensor(s) 170 of the personal care device 102 capture image data of the region of interest 120, and the system 100 compares this captured data with texture data mapped to the reference points 210. If sufficient matches are found between the captured data and the reference points 210, the system 100 is able to calculate a relative position of the personal care device 102 based on the known position of the reference points 210 in the 3D model. Meanwhile, data captured by the camera unit 150 of the client computing device 104 is used to locate the personal care device 102 anatomically.

In some embodiments, the arrangement described with reference to FIGS. 1 and 2 is useful for adapting techniques described herein to changes in skin condition or other changes in the body surface 110 (e.g., weight loss, weight gain, sagging, changes in facial expression, etc.) For example, a deeply furrowed brow may change the location of reference points 210 relative to one another if the 3D model was originally based on a relaxed facial expression as a baseline, or vice versa. Because the reference points 210 can be identified with a matching process, rather than just by location, the location of the personal care device 102 relative to the reference points 210 can still be identified even if the reference points 210 have shifted (e.g., by moving closer together or further apart from one another) either temporarily (e.g., based on a change of expression or other temporary perturbation of the skin) or on a more permanent basis (e.g., due to weight loss, weight gain, sagging, etc.). In an embodiment, skin physics modeling software is used to simulate what happens to the target coordinate as posture (e.g., facial expression) changes or when an object presses into the skin surface. If present, skin physics modeling software may be implemented in client computing device 104 or a remote computer system, or on some other computing device or system.

Other adaptations can be performed for variations in lighting conditions, viewing angles, or other factors. As one example, a light sensor mounted on the client computing device 104 or the personal care device 102 can be used to measure current lighting conditions relative to a baseline lighting condition. If the environment is too bright or too dark, it may be difficult to find sufficient matches for reference points. In an embodiment, the client computing device 104 or personal care device 102 may provide feedback to a user (e.g., via synthesized voice cues or visual indicators) to adjust the lighting conditions for better results. In another scenario, the personal care device 102 is not recognized in the field of view 152 of the camera unit 150. In an embodiment, the client computing device 104 or personal care device 102 provides feedback to a user (e.g., via synthesized voice cues or visual indicators) in this scenario to adjust the viewing angle of the camera unit 150 or to bring the personal care device into the field of view 152 for better results.

It should be understood that described embodiments are capable of implementation in many possible ways to determine matches between captured image data and texture data in a 3D model, including matching detected edges or contours, color/pixel values, depth information, or the like in different combinations, and at particular threshold levels of confidence, any of which may be adjusted based on lighting conditions, user preferences, system design constraints, or other factors.

In some embodiments, the system 100 causes the skin interaction unit 160 of the personal care device 102 to perform one or more actions (e.g., applying a skin treatment, applying cosmetics, mapping skin features, etc.) based on the determined position of the personal care device 102, as described in further detail below with reference to FIG. 3. In some embodiments, such interactions are performed while the personal care device 102 is in motion (e.g., during a cosmetics application routine, a skin treatment routine, or some other care routine).

Figure 3:
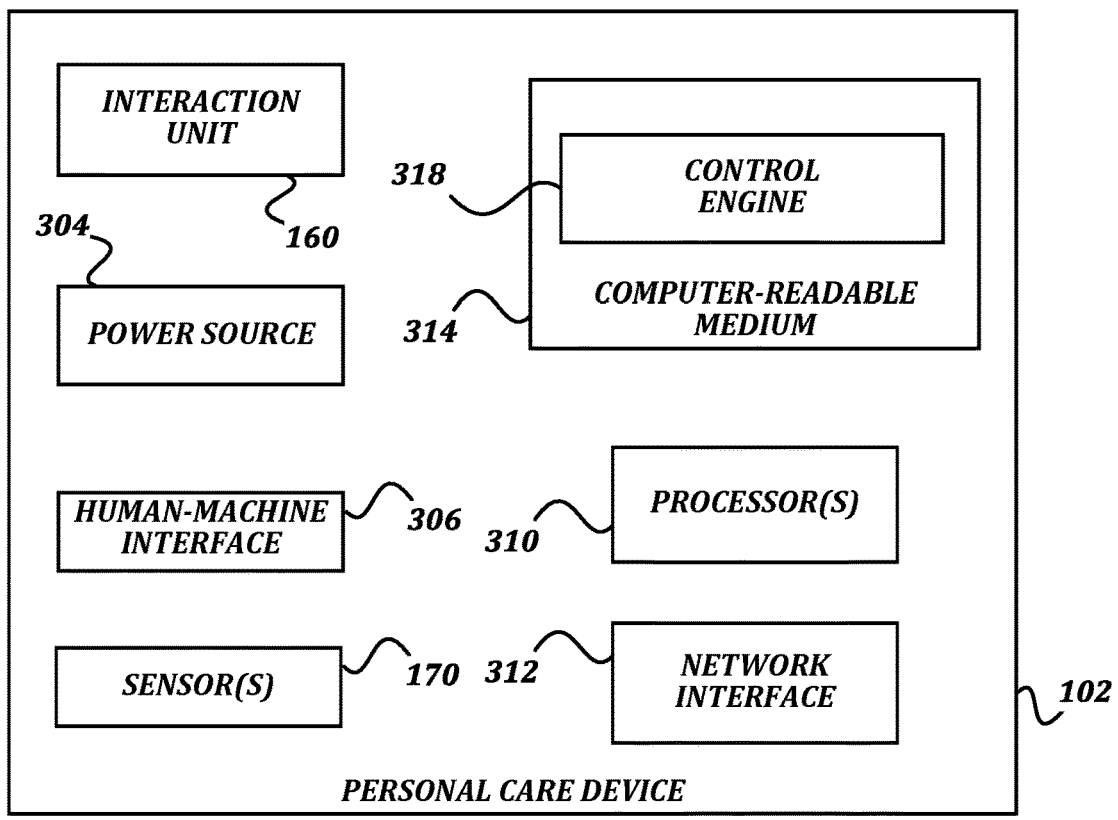
FIG. 3 is a block diagram that illustrates components included in an embodiment of a personal care device, according to various aspects of the present disclosure.

FIG. 3 is a block diagram that illustrates components included in an example embodiment of a personal care device 102 according to various aspects of the present disclosure. FIG. 3 depicts a non-limiting example of personal care device features and configurations; many other features and configurations are possible within the scope of the present disclosure.

In the example shown in FIG. 3, the personal care device 102 includes an interaction unit 160, one or more sensors 170, a power source 304, a human-machine interface device 306, one or more processors 310, a network interface 312, and a computer-readable medium 314.

The interaction unit 160 is configured to interact with a body surface. In an embodiment, the interaction unit 160 comprises a cosmetic application unit including microfluidic jets or some other mechanism for applying makeup, body paint, or another substance to a body surface. In an embodiment, applied cosmetics or substances other than cosmetics (e.g., tracking dots, graphical codes, or other distinctive patterns) provide additional reference points for additional accuracy in location tracking.

In another embodiment, the interaction unit 160 includes one or more devices that apply a skin treatment to a user. As one example, the interaction unit 160 may include a drive motor, an armature coupled to the drive motor that accepts a detachable brush head, and the brush head itself. As another example, the interaction unit 160 may include one or more light-emitting diodes (LEDs) or other light-emitting devices that emit light of suitable wavelengths and intensity for phototherapy applications.

In an embodiment, the sensors 170 include a depth sensor, and the detecting of the relative location of the personal care device is based at least in part on depth data obtained from the depth sensor, e.g., by comparing the depth data with a corresponding portion of a 3D model. In an embodiment, the sensors 170 include a proximity sensor, and the detecting of the location of the personal care device is based at least in part on data obtained from the proximity sensor.

In an embodiment, the power source 304 is a rechargeable battery that provides power for operation of the interaction unit 160 and the other components of the personal care device 102. In other embodiments, instead of a battery, the skin care device 102 may be coupled to an external power source, such as an electrical outlet.

The human-machine interface (HMI) 306 may include any type of device capable of receiving user input or generating output for presentation to a user, such as a speaker for audio output, a microphone for receiving audio commands, a push-button switch, a toggle switch, a capacitive switch, a rotary switch, a slide switch, a rocker switch, or a touch screen.

The processor 310 is configured to execute computer-executable instructions stored on the computer-readable medium 314. In an embodiment, the processor 310 is configured to receive and transmit signals to and/or from other components of the personal care device 102 via a communication bus or other circuitry. The network interface 312 is configured to transmit and receive signals to and from the client computing device 104 (or other computing devices) on behalf of the processor 310. The network interface 312 may implement any suitable communication technology, including but not limited to short-range wireless technologies such as Bluetooth, infrared, near-field communication, and Wi-Fi; long-range wireless technologies such as WiMAX, 2G, 3G, 4G, LTE, and 5G; and wired technologies such as USB, FireWire, and Ethernet. The computer-readable medium 314 is any type of computer-readable medium on which computer-executable instructions may be stored, including but not limited to a flash memory, a ROM, an EPROM, an EEPROM, and an FPGA. The computer-readable medium 314 and the processor 310 may be combined into a single device, such as an ASIC, or the computer-readable medium 314 may include a cache memory, a register, or another component of the processor 310.

In the illustrated embodiment, the computer-readable medium 314 has computer-executable instructions stored thereon that, in response to execution by one or more processors 310, cause the personal care device 102 to implement a control engine 318. The control engine 318 controls one or more aspects of the personal care device 102 in a care routine, as described above. In an embodiment, the computer-executable instructions are configured to cause the personal care device 102 to perform one or more actions such as application of a cosmetic product (e.g., makeup, nail polish, etc.), or detection of a skin feature, or administration of a therapy at a precise location of the human body surface based on the true position of the personal care device 102. In an embodiment, the control engine 318 controls basic functions such as turning the treatment application unit on or off, controlling the interaction unit 160, or controlling the sensors 170 according to techniques described herein. In an embodiment, the control engine 318 detects input from HMI 306 indicating that a care routine is to be initiated (e.g., in response to activation of a power switch or "start" button), receives signals from the client computing device 104, or some other computing device relating to activation of the interaction unit at a determined position, and activates the interaction unit 160 at the determined position in response to the received signals. The control engine 318 may then detect a subsequent input from the HMI 306 and deactivate the interaction unit 160 or make further adjustments to the function of the personal care device 102.

The interaction unit 160 and the sensor(s) 170 need not both be present. For example, in an embodiment the personal care device 102 is designed for mapping skin features of the body surface 110, and the sensor(s) 170 and/or other sensors are used for obtaining image data and/or depth data to serve this purpose. In such an embodiment, the interaction unit 160 can be deactivated or omitted.

In an embodiment where the sensors 170 include a proximity sensor, the data obtained from the proximity sensor may be used to determine whether the personal care device 102 is within a predetermined distance of the body surface before performing an interaction. This can be useful in situations where the personal care device 102 is determined to be in the correct location relative to known reference points in an X-Y plane, but may be too far from the body surface 110 to effectively perform a desired action such as applying a cosmetic product or performing a skin treatment. In an illustrative scenario, a maximum distance for a desired interaction is stored in memory, and if the personal care device 102 is determined to be further from the body surface than the maximum distance, the personal care device 102 or the client computing device 104 provides feedback (e.g., visual, audio, or haptic feedback) to a user to prompt the user move the personal care device 102 closer to the body surface before the interaction is performed.

Alternatively, the personal care device 102 includes different components or circuitry, or the components and circuitry described with reference to FIG. 3 are implemented in some other way.

Figure 4:
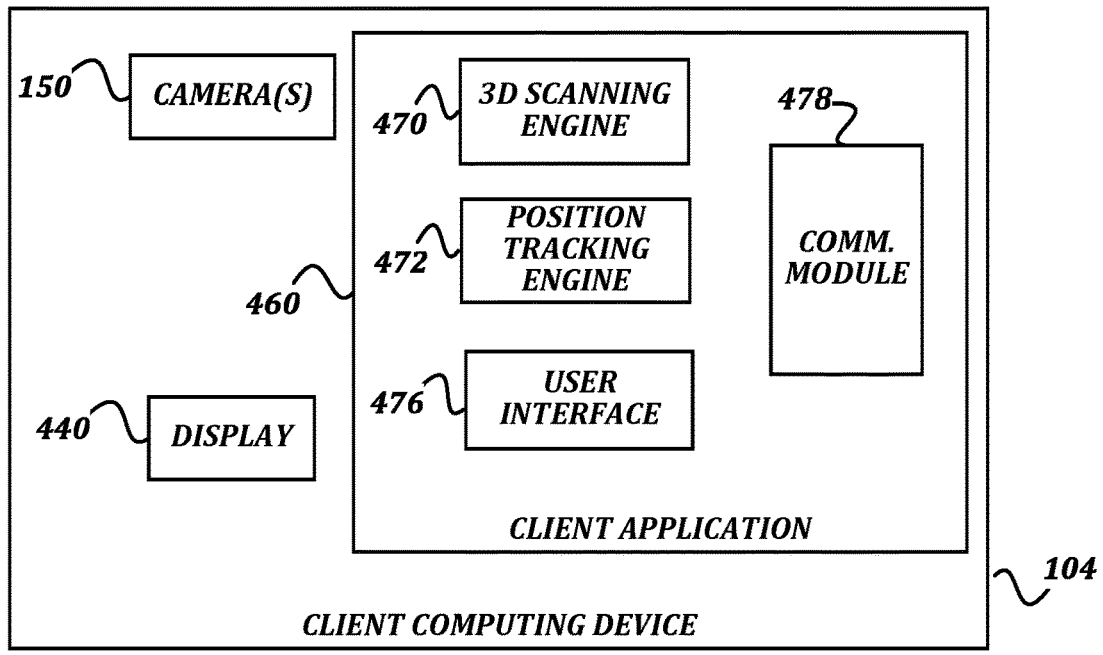
FIG. 4 is a block diagram that illustrates an embodiment of a client computing device according to various aspects of the present disclosure.

FIG. 4 is a block diagram that illustrates an example embodiment of a client computing device 104 according to various aspects of the present disclosure. FIG. 4 depicts a non-limiting example of client computing device features and configurations; many other features and configurations are possible within the scope of the present disclosure.

In the example shown in FIG. 4, the client computing device 104 includes a camera unit 150 comprising one or more cameras and a client application 460. The client application 460 includes a user interface 476. In an embodiment, the user interface 476 includes interactive functionality such as graphical guides to assist a user in positioning the camera unit 150 correctly, tutorial videos or animations, or other elements. Visual elements of the user interface 476 are presented on a display 440, such as a touchscreen display. In an embodiment, the user interface provides 476 guidance (e.g., visual guides such as arrows or targets, progress indicators, audio/haptic feedback, synthesized speech, etc.) to guide a user to take images under particular lighting conditions, angles, etc., in order to ensure that sufficient data is collected to, e.g., track the position of the personal care device 102.

In an embodiment, the client application 460 also includes and image capture/3D scanning engine 470 configured to capture and process digital images (e.g., color images, infrared images, depth images, etc.) obtained from camera unit 150. In an embodiment, such images are used to obtain a clean and precise 3D contour mapping of the target body surface (e.g., a face). In an embodiment, the digital images or scans are processed by the client computing device 104 and/or transmitted to a remote computer system for processing in a 3D model engine. In an embodiment, captured image data is used in position tracking engine 472 for determining the position of a personal care device 102 relative to a body surface. In an embodiment, the position tracking engine 472 maintains precise awareness of where the target body surface 110 is and where the personal care device 102 is in a 3D space, even when the personal care device 102 is partially obscured. In an embodiment, position information from the position tracking engine 472 is used to generate signals to be transmitted to the control engine 318, which are used to control the interaction unit 160 and/or sensors 170 of the personal care device 102, according to techniques described herein.

In an embodiment, digital 3D models described herein are generated based on sensor data obtained the client computing device 104. In such an embodiment, the digital 3D models are generated by the client computing device 104 or some other computing device, such as a remote cloud computing system, or a combination thereof. In embodiment, the digital 3D models include 3D topology and texture information, which can be used for reproducing an accurate representation of a body surface, such as facial structure and skin features.

In an embodiment, a communication module 478 of the client application 460 is used to prepare information for transmission to, or to receive and interpret information from other devices or systems, such as a remote computer system or a personal care device 102. Such information may include captured digital images, scans, or video, personal care device settings, custom care routines, user preferences, user identifiers, device identifiers, or the like.

Other features of client computing devices are not shown in FIG. 4 for ease of illustration. Alternatively, the client computing device 104 includes different components or circuitry, or the components and circuitry described with reference to FIG. 4 are implemented in some other way.

Further description of illustrative computing devices is provided below with reference to FIG. 7.

Figure 5:
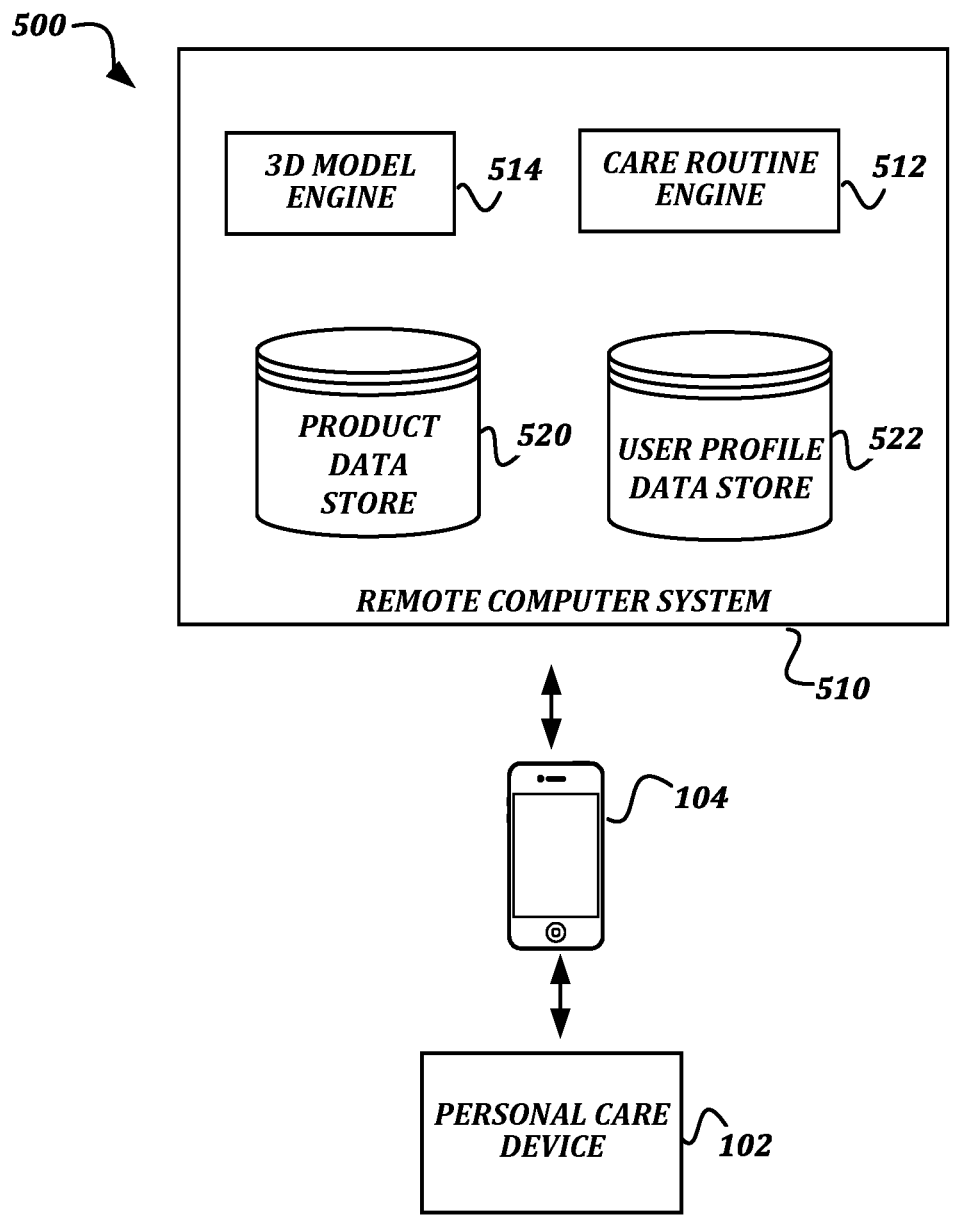
FIG. 5 is a block diagram that illustrates a computer system including a remote computer system, a client computing device, and a personal care device, in which various aspects of the present disclosure may be implemented.

FIG. 5 is a block diagram that illustrates a system 500 in which various aspects of the present disclosure may be implemented. A client computing device 104 connects to and communicates with a remote computer system 110 and a personal care device 102. In an embodiment, custom routines or device settings may be uploaded to the client computing device 104 for subsequent transmission to the personal care device 102.

In an embodiment, the personal care device 102 collects data describing execution of care routines, image data of body surfaces, or other data. In an embodiment, such data is transmitted via the network interface 312 to the mobile computer device 104 or a remote computer system 510 for further processing or storage (e.g., in a product data store 520 or user profile data store 522). The client computing device 104 may be used by a consumer, personal care professional, or some other entity to interact with other components of the system 500, such as the remote computer system 510 or personal care device 102. In an embodiment, the client computing device 104 is a mobile computing device such as a smartphone or a tablet computing device.

Illustrative components and functionality of the remote computer system 510 will now be described. The remote computer system 510 includes one or more server computers that implement one or more of the illustrated components, e.g., in a cloud computing arrangement. As illustrated in FIG. 5, the remote computer system 510 includes a care routine engine 512, a 3D model engine 514, a product data store 520, and a user profile data store 522. In an embodiment, the 3D model engine 514 uses image data (e.g., color image data, infrared image data) and depth data to generate a 3D model of a body surface. The image data is obtained from one or mor image sensors, and depth data is obtained from one or depth sensors. In some embodiments, such sensors are integrated with or otherwise in communication with client computing device 104, personal care device 102, or a combination thereof. In an embodiment, image data and depth data associated with a user is stored in the user profile data store 522. In an embodiment, user consent is obtained prior to storing any information that is private to a user or can be used to identify a user. may be stored.

In an embodiment, the care routine engine 512 performs processing of data relating to a care routine, such as identifying changes in skin condition or generating a computer-guided care routine, which can then be transmitted to, e.g., the client computing device 104 and/or the personal care device 102. The guided care routine information may include, for example, programmatic care routine instructions for performing a care routine, collecting data (e.g., image data, depth data, usage data, or other data), or performing other functions according to techniques described herein. In an embodiment, the care routine engine 112 generates guided care routine information based on user information from the user profile data store 122, the product data store 120, or some other source or combination of sources. The care routine engine 112 may employ machine learning or artificial intelligence techniques (e.g., template matching, feature extraction and matching, classification, artificial neural networks, deep learning architectures, genetic algorithms, or the like). For example, to generate a custom care routine, the care routine engine 112 may analyze digital scans to measure or map wrinkles, pigmentation, skin texture, etc., of the user's skin. In such a scenario, the care routine engine 112 may use such information to recommend, generate or modify a particular care routine that suits the particular features of the user's skin.

The devices shown in FIGS. 1, 3, 4, and 5, or other devices used in described embodiments may communicate with each other via a network (not shown), which may include any suitable communication technology including but not limited to wired technologies such as DSL, Ethernet, fiber optic, USB, and Firewire; wireless technologies such as WiFi, WiMAX, 3G, 4G, LTE, 5G, and Bluetooth; and the Internet. In general, communication between computing devices or components in FIGS. 1, 3, 4, and 5, or other components or computing devices used in accordance with described embodiments, occur directly or through intermediate components or devices.

Many alternatives to the arrangements disclosed and described with reference to FIGS. 1, 3, 4, and 5, are possible. For example, functionality described as being implemented in multiple components may instead be consolidated into a single component, or functionality described as being implemented in a single component may be implemented in multiple illustrated components, or in other components that are not shown in FIG. 1, 3, 4, or 5. As another example, devices in FIGS. 1, 3, 4, and 5 that are illustrated as including particular components may instead include more components, fewer components, or different components without departing from the scope of described embodiments. As another example, functionality that is described as being performed by a particular device may instead be performed by one or more other devices within a system. As an example, the 3D model engine 514 may be implemented in client computing device 104 or in some other device or combination of devices.

In addition to the technical benefits of described embodiments that are described elsewhere herein, numerous other technical benefits are achieved in some embodiments. For example, the system 500 allows some aspects of the process to be conducted independently by personal care devices or client computing devices, while moving other processing burdens to the remote computer system 510 (which may be a relatively high-powered and reliable computing system), thus improving performance and preserving battery life for functionality provided by personal care devices or client computing devices. In general, the word "engine," as used herein, refers to logic embodied in hardware or software instructions written in a programming language, such as C, C++, COBOL, JAVA™, PHP, Perl, HTML, CSS, JavaScript, VBScript, ASPX, Microsoft.NET™, and/or the like. An engine may be compiled into executable programs or written in interpreted programming languages. Software engines may be callable from other engines or from themselves. Generally, the engines described herein refer to logical modules that can be merged with other engines or divided into sub-engines. The engines can be stored in any type of computer-readable medium or computer storage device and be stored on and executed by one or more general purpose computers, thus creating a special purpose computer configured to provide the engine or the functionality thereof.

As understood by one of ordinary skill in the art, a "data store" as described herein may be any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, as described further below. One of ordinary skill in the art will recognize that separate data stores described herein may be combined into a single data store, and/or a single data store described herein may be separated into multiple data stores, without departing from the scope of the present disclosure.

Figure 6:
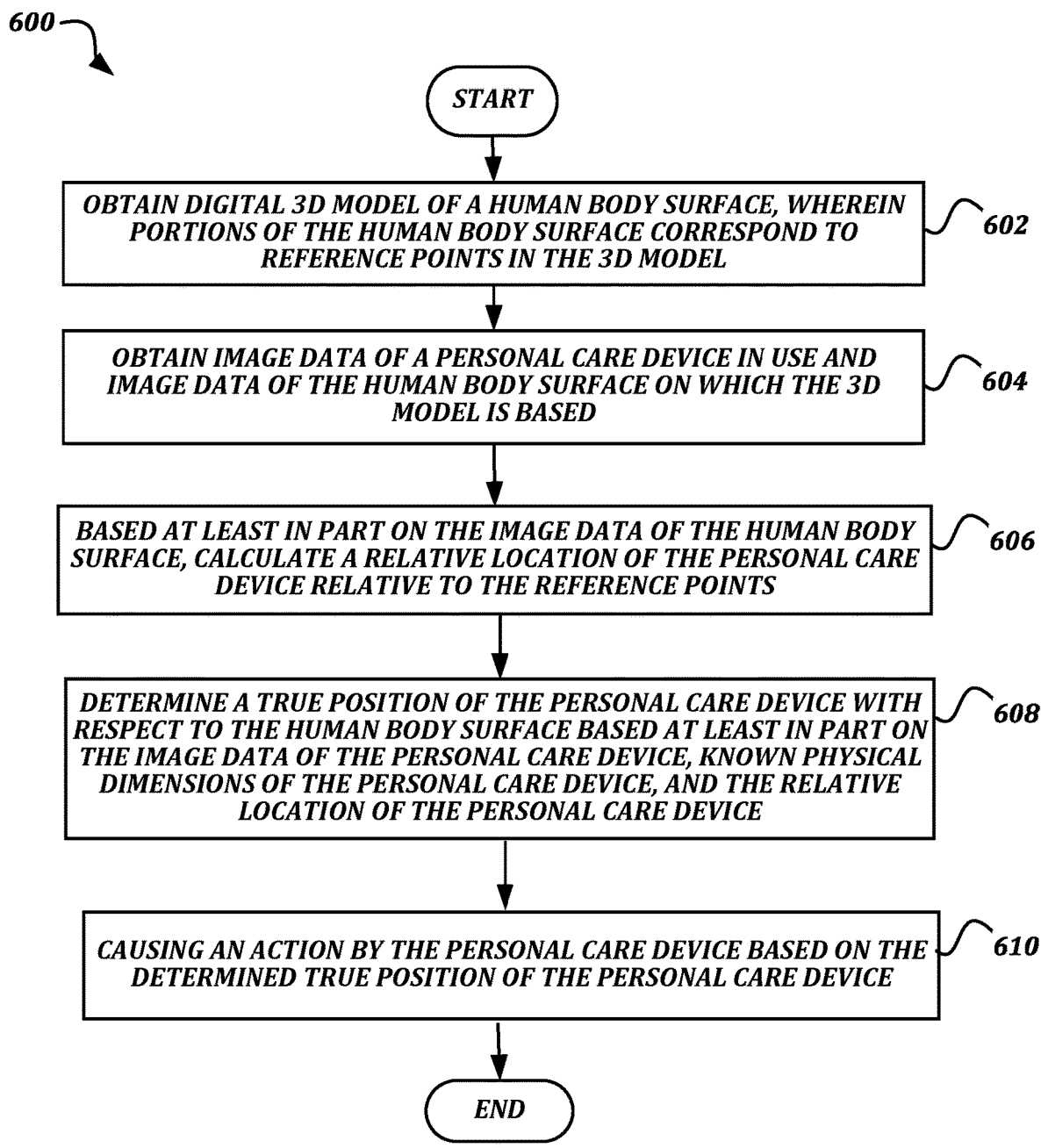
FIG. 6 is a flowchart that illustrates an embodiment of a method of determining a true position of a personal care device in use in relation to a body surface, according to various aspects of the present disclosure.

FIG. 6 is a flowchart that illustrates an embodiment of a method of determining a true position of a personal care device in use in relation to a body surface, according to various aspects of the present disclosure. The method 600 is performed by a computer system including one or more computing devices, such as client computing device 104, personal care device 102, or some other computing device or combination of devices.

At block 602, a computer system obtains a digital 3D model of a human body surface, such as a face or other region of interest. Portions of the human body surface are modeled in corresponding portions of the digital 3D model, which act as reference points. These reference points need not be artificial reference points such as graphical codes and need not be traditional facial features such as eyes or lips. Instead, in an embodiment, the reference points include any distinctive sets of color values, depth values, 3D contour segments, or combinations thereof at particular 3D coordinates in the model.

At block 604, the computer system obtains image data of a personal care device in use and the human body surface on which the digital 3D model is based. In an embodiment, the computer system obtains the image data of the personal care device from one or more image sensors separate from the personal care device (e.g., from camera unit 150 on a client computing device 104 or some other camera or set of cameras). Alternatively, the computer system obtains the image data of the personal care device in use from one or more image sensors mounted on the personal care device. In an embodiment, referring again to FIG. 1, such a sensor is mounted on the back end of the personal care device 102, opposite to and facing the front end, on which the interaction unit 160 is mounted.

At block 606, the computer system calculates a relative location of the personal care device relative to the reference points based at least in part on the image data of the human body surface. In an embodiment, the computer system uses a matching process that compares the image data with corresponding reference points in the digital 3D model to determine the relative location of the personal care device. In an embodiment, the image data is obtained at least in part by one or more image sensors separate from the personal care device, such as by one or more cameras mounted on a mobile computing device.

At block 608, the computer system determines a true position of the personal care device with respect to the human body surface based at least in part on the image data of the personal care device in use, the known physical dimensions of the personal care device, and the relative location of the personal care device relative to the reference points.

At block 610, the computer system causes an interaction with the human body surface by the personal care device based on the determined true position of the personal care device. In an illustrative scenario, the interaction includes application of a cosmetic product or other substance to the skin surface or administration of a skin therapy during a computer-guided care routine.

Many alternatives to the process depicted in FIG. 6 are possible, in accordance with embodiments described herein. In an illustrative scenario where the personal care device is being used as a scanning device to obtain image or depth information to map the body surface or detect features of the body surface, further steps of processing or transmitting the captured image and/or depth information to another computing device (e.g., client computing device 104) are performed, and process block 610 is omitted if no physical interaction with the body surface is being performed.

Figure 7:
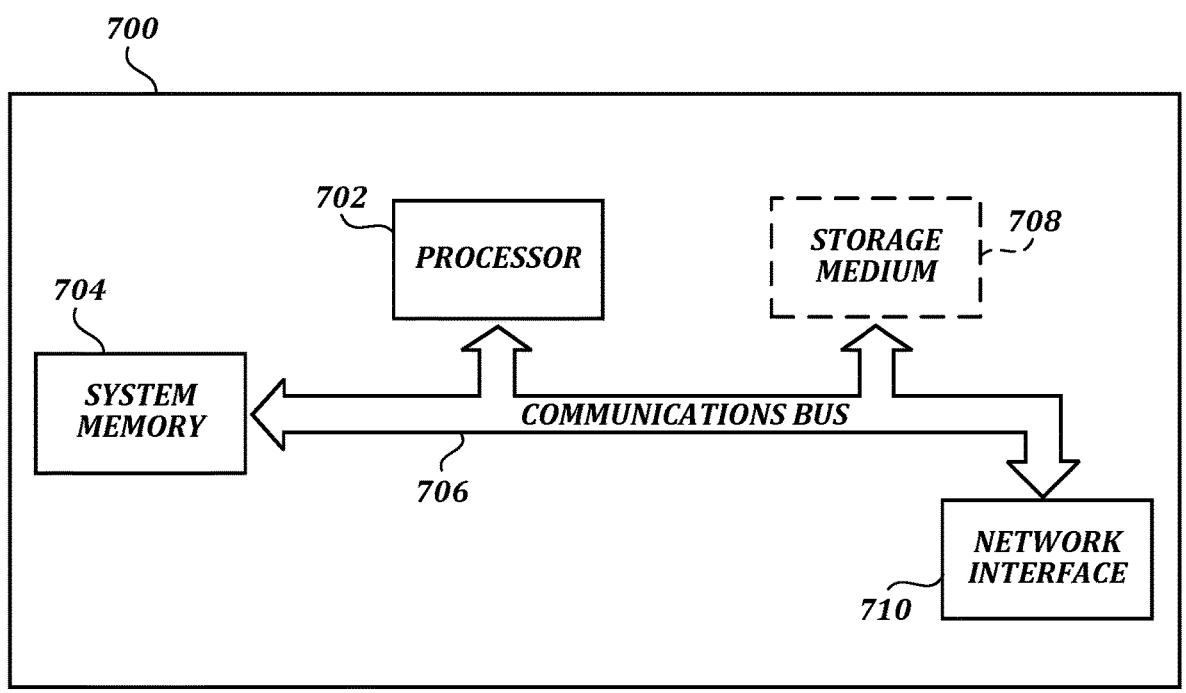
FIG. 7 is a block diagram that illustrates aspects of an illustrative computing device appropriate for use as a computing device of the present disclosure.

FIG. 7 is a block diagram that illustrates aspects of an exemplary computing device 700 appropriate for use as a computing device of the present disclosure. While multiple different types of computing devices were discussed above, the exemplary computing device 700 describes various elements that are common to many different types of computing devices. While FIG. 7 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 700 may be any one of any number of currently available or yet to be developed devices.

In its most basic configuration, the computing device 700 includes at least one processor 702 and a system memory 704 connected by a communication bus 706. Depending on the exact configuration and type of device, the system memory 704 may be volatile or nonvolatile memory, such as read only memory ("ROM"), random access memory ("RAM"), EEPROM, flash memory, or similar memory technology. Those of ordinary skill in the art and others will recognize that system memory 704 typically stores data and/or program modules that are immediately accessible to and/or currently being operated on by the processor 702. In this regard, the processor 702 may serve as a computational center of the computing device 700 by supporting the execution of instructions.

As further illustrated in FIG. 7, the computing device 700 may include a network interface 710 comprising one or more components for communicating with other devices over a network. Embodiments of the present disclosure may access basic services that utilize the network interface 710 to perform communications using common network protocols. The network interface 710 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 710 illustrated in FIG. 7 may represent one or more wireless interfaces or physical communication interfaces described and illustrated above with respect to particular components of the system 100.

In the exemplary embodiment depicted in FIG. 7, the computing device 700 also includes a storage medium 708. However, services may be accessed using a computing device that does not include means for persisting data to a local storage medium. Therefore, the storage medium 708 depicted in FIG. 7 is represented with a dashed line to indicate that the storage medium 708 is optional. In any event, the storage medium 708 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 704 and storage medium 708 depicted in FIG. 7 are merely examples of computer-readable media.

Suitable implementations of computing devices that include a processor 702, system memory 704, communication bus 706, storage medium 708, and network interface 710 are known and commercially available. For ease of illustration and because it is not important for an understanding of the claimed subject matter, FIG. 7 does not show some of the typical components of many computing devices. In this regard, the computing device 700 may include input devices, such as a keyboard, keypad, mouse, microphone, touch input device, touch screen, and/or the like. Such input devices may be coupled to the computing device 700 by wired or wireless connections including RF, infrared, serial, parallel, Bluetooth, Bluetooth low energy, USB, or other suitable connections protocols using wireless or physical connections. Similarly, the computing device 700 may also include output devices such as a display, speakers, printer, etc. Since these devices are well known in the art, they are not illustrated or described further herein.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method comprising:
   obtaining, by one or more cameras of a computing device, image data of a personal care device and image data of a human body surface;
   generating a digital representation on a display of a 3-dimensional model including a plurality of reference locations on the human body surface based at least in part on the image data of the human body surface;
   determining a relative location of the personal care device relative to the plurality of reference locations on the human body surface;
   generating a digital representation of a true position of the personal care device with respect to the human body surface based at least in part on the image data of the personal care device, pre-determined physical dimensions of the personal care device, and the relative location of the personal care device; and
   causing an interaction of the personal care device with a corresponding portion of the human body surface, wherein the interaction includes application of a cosmetic product or administration of a skin therapy.

2. The method of claim 1, wherein the image data of the human body surface is further obtained from one or more image sensors mounted on the personal care device.

3. The method of claim 1, wherein the generating of the digital representation of the true position of the personal care device is further based on depth data obtained from one or more depth sensors or proximity data obtained from one or more proximity sensors or a combination thereof.

4. The method of claim 1, wherein the interaction occurs as the personal care device is in motion.

5. The method of claim 1 further comprising detecting one or more skin features at a corresponding portion of the human body surface based at least in part on the image data of the human body surface.

6. The method of claim 5 further comprising adding the one or more detected skin features to a map of skin features of the human body surface.

7. The method of claim 1, wherein the human body surface comprises at least part of a face.

8. A non-transitory computer-readable medium having stored thereon computer-executable instructions configured to cause a computer system comprising one or more computing devices to perform steps comprising:
   obtaining a digital 3-dimensional model of a human body surface, wherein portions of the human body surface correspond to reference points in the digital 3-dimensional model;
   obtaining image data of a personal care device and image data of the human body surface on which the digital 3-dimensional model is based, wherein the image data of the personal care device and the image data of the human body surface is captured by one or more cameras of a computing device separate from the personal care device;
   based at least in part on the image data of the human body surface, calculating a relative location of the personal care device relative to the reference points;
   determining a true position of the personal care device with respect to the human body surface based at least in part on the image data of the personal care device, pre-determined physical dimensions of the personal care device, and the relative location of the personal care device; and
   based on the true position of the personal care device, cause an interaction of the personal care device with the human body surface, wherein the interaction includes application of a cosmetic product or administration of a skin therapy.

9. The non-transitory computer-readable medium of claim 8, wherein the image data of the human body surface is further obtained from one or more image sensors mounted on the personal care device.

10. The non-transitory computer-readable medium of claim 8, wherein the calculating of the relative location of the personal care device is further based on depth data obtained from a depth sensor or proximity data obtained from a proximity sensor or a combination thereof.

11. The non-transitory computer-readable medium of claim 8, wherein the interaction occurs as the personal care device is in motion.

12. The non-transitory computer-readable medium of claim 8, wherein the computer-executable instructions are further configured to cause the computer system to detect one or more skin features at a corresponding portion of the human body surface based at least in part on the image data of the human body surface.

13. The non-transitory computer-readable medium of claim 12, wherein the computer-executable instructions are further configured to cause the computer system to add the one or more detected skin features to a map of skin features of the human body surface.

14. The non-transitory computer-readable medium of claim 8, wherein the human body surface comprises at least part of a face.

15. A personal care device comprising one or more sensors, at least one processor, and memory, the memory having stored therein computer-executable instructions configured to cause the personal care device to perform steps comprising:

obtaining, via the one or more sensors, sensor data with respect to a human body surface on which a digital 3-dimensional model is based, wherein portions of the human body surface correspond to reference points in the digital 3-dimensional model;

based at least in part on the sensor data obtained via the one or more sensors, calculating a relative location of the personal care device relative to the reference points in the digital 3-dimensional model; and determining a true position of the personal care device with respect to the human body surface based at least in part on image data of the personal care device in use, pre-determined physical dimensions of the personal care device, and the relative location of the personal care device, wherein the image data of the personal care device is captured by one or more cameras of a computing device separate from the personal care device; and based on the true position of the personal care device, performing application of a cosmetic product, or detection of a skin feature, or administration of a therapy.

16. The personal care device of claim 15 wherein the one or more sensors include a depth sensor, and wherein the detecting of the relative location of the personal care device is based on depth data obtained from the depth sensor.

17. The personal care device of claim 15 wherein the one or more sensors include a camera, and wherein the detecting of the relative location of the personal care device is based on image data obtained from the camera.

18. A system comprising:

a surface features unit operably coupled to a plurality of sensors, the surface features unit including computational circuitry and at least one processor configured to obtain sensor data with respect to a human body surface, and generate a digital representation on a display of a 3-dimensional model including a plurality of reference locations on a human body surface; and a locator unit operably coupled to the surface features unit and a personal care device, the locator unit including computational circuitry and at least one processor configured to determine a location of a personal care device relative to one or more of the plurality of reference locations on the human body surface; and determine a true position of the personal care device relative to the human body surface based at least in part on image data of the personal care device in use, pre-determined physical dimensions of the personal care device, and the relative location of the personal care device, wherein the image data of the personal care device is captured by one or more cameras of a computing device separate from the personal care device; and circuitry configured to cause an interaction of the personal care device with a corresponding portion of the human body surface, wherein the interaction includes application of a cosmetic product or administration of a skin therapy.

19. The system of claim 18, wherein the locator unit operably coupled to the surface features unit and the personal care device includes computational circuitry and at least one processor configured to determine the orientation of the personal care device relative to one or more of the plurality of reference locations on the human body surface based at least in part on image data of the personal care device in use, pre-determined physical dimensions of the personal care device, and the relative location of the personal care device.

20. The system of claim 18, wherein the locator unit operably coupled to the surface features unit and the personal care device includes computational circuitry and at least one processor configured to determine relative movement information of the personal care device relative to one or more of the plurality of reference locations on the human body surface based at least in part on image data of the personal care device in use, pre-determined physical dimensions of the personal care device, and the relative location of the personal care device.

* * * * *